United States Patent [19]

Ambrosio et al.

[11] 4,317,446

[45] Mar. 2, 1982

[54] PREFILLED DISPOSABLE SYRINGE

[75] Inventors: Thomas J. Ambrosio, Somerville; Henry J. Buchman, Edison; Joseph J. Rogus, Bridgewater; Henry R. Sochon, Clifton, all of N.J.

[73] Assignee: Schering Corporation, Kenilworth, N.J.

[21] Appl. No.: 183,916

[22] Filed: Sep. 4, 1980

[51] Int. Cl.³ .............................................. A61M 5/00
[52] U.S. Cl. .................................. 128/218 R; 128/221
[58] Field of Search ......... 128/218 R, 218 P, 218 PA, 128/221, 215, 234

[56] References Cited

U.S. PATENT DOCUMENTS

| 2,693,803 | 11/1954 | Ogle | 128/218 P |
| 3,545,607 | 12/1970 | Keller | 128/218 P |
| 4,248,246 | 2/1981 | Ikeda | 128/218 R X |

FOREIGN PATENT DOCUMENTS 2401665  4/1979  France ........................ 128/218 PA Primary Examiner—John D. Yasko
Attorney, Agent, or Firm—Warrick E. Lee, Jr.; Vincent H. Gifford; Bruce M. Eisen

[57] ABSTRACT

A prefilled disposable syringe having a barrel, hub, and needle with a plunger rod/protector attached to the outer surface of the barrel near the hub by flexible protrusions from the inner surface of the plunger rod/protector. The flexible protrusions frictionally engage the outer surface.

16 Claims, 4 Drawing Figures

PREFILLED DISPOSABLE SYRINGE

BACKGROUND

This invention relates to disposable syringes, more specifically, to syringes having a needle protector capable of functioning as a plunger rod after it has been removed from its position protectng the needle and attached to a stopper disposed in the syringe's barrel.

The present invention has several advantages over prior-art syringes wherein the plunger rod/protector is attached at the syringe hub by a force fit over a sheath. The needle is far less likely to be bent during shipment and handling. The syringe barrel is protected at the place where it is most likely to break. The needle sheath will not be removed accidentally when the plunger rod/protector is removed from its protective position. The plunger rod/protector fits well despite normal dimensional variation in a glass syringe barrel.

One aspect of the present invention is a prefilled disposable syringe comprising:

(a) an assembly having a hub, a needle rigidly attached to the hub, and a barrel having a hollow bore and an outer surface near the hub, (b) a stopper disposed in the bore having first engagement means, (c) medicament disposed in the bore between the stopper and the needle, and (d) a plunger rod/protector adapted to enclose the needle, hub and outer surface comprising a narrow portion having a cavity for the needle, the narrow portion capable of fitting within the hollow bore; attachment means for attaching the plunger rod/protector to the outer surface at a first end of the narrow portion comprising an inner surface adapted to enclose the outer surface and flexible means protruding from the inner surface to grip the outer surface; and a second engagement means at a second end of the narrow portion adapted to engage the first engagement means, wherein the plunger rod/protector is adapted to securely protect the needle during transit and storage and to act as a plunger rod after engagement of the first and second engagement means.

Other aspects of the invention comprise a syringe suitable for prefilling and a plunger rod/protector.

DETAILED DESCRIPTION OF THE INVENTION

Figure 1:
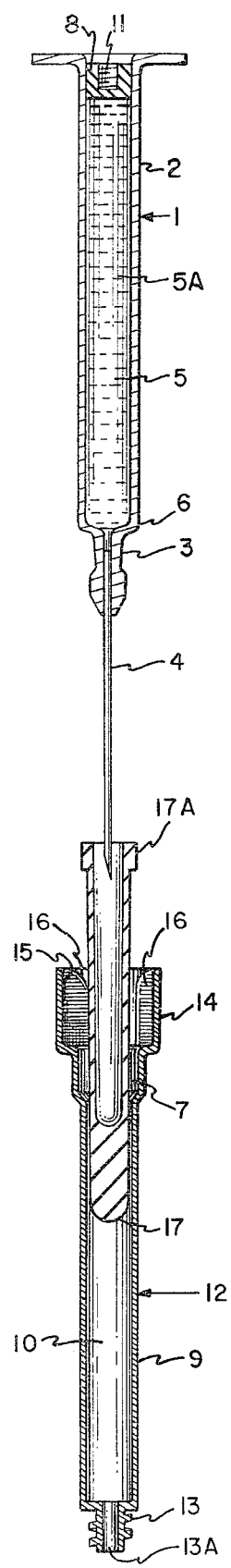
FIG. 1 is a longitudinal cross-sectional view of a prefilled disposable syringe in accordance with the invention with the plunger rod/protector and needle sheath shown separated.

Referring to FIG. 1, assembly 1 comprises barrel 2, preferably made of glass for long term storage, integral hub 3, and needle 4 rigidly affixed to hub 3.

Barrel 2 has hollow bore 5 in fluid communication with the needle. Medicament 5A is disposed in the hollow bore between the needle and stopper 8. Stopper 8 has a first engagement means 11, preferably an inner thread. Barrel 2 has outer surface 6 near hub 3.

A plunger rod/protector 12 is adapted to enclose needle 4, hub 3, and outer surface 6 during shipment and storage. Plunger rod/protector 12 has a narrow portion 9 having a cavity 10 for needle 4. The narrow portion is capable of fitting within hollow bore 5.

At a first end of narrow portion 9 of plunger rod/protector 12, there is located attachment means 14 for attaching the plunger rod/protector to outer surface 6. Attachment means 14 comprises an inner surface 15 adapted to enclose outer surface 6 and flexible means 16 protruding from the inner surface. At a second end of the narrow portion of plunger rod/protector 12, there is located a second engagement means 13 adapted to engage first engagement means 11.

Preferably plunger rod/protector 12 is a molded plastic material such as polypropylene, polyethylene, polyamide, polyacrylonitrile, or copolymers thereof. Preferably the mold used to cast the plunger rod/protector has a central rod affixed at both ends to shape cavity 10. This way the rod cannot flex during casting, causing the cavity to be eccentric. This method of casting produces an inner bore 13A in second engagement means 13.

To maintain sterility and seal needle 4, it is preferable to cover and seal needle 4 with elastomeric needle sheath 17. A needle sheath normally has a shoulder 17A located at its open end.

Figure 2:
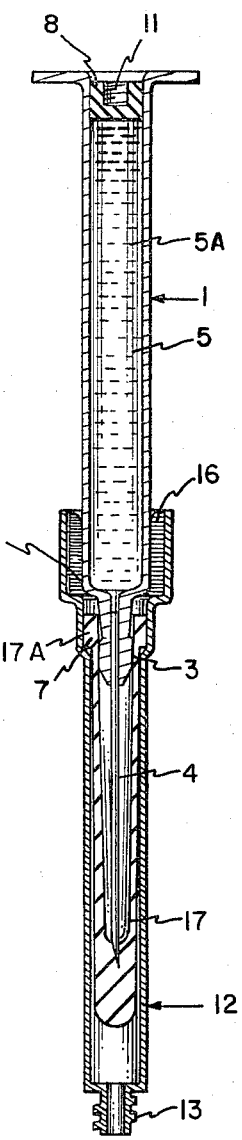
FIG. 2 is a longitudinal cross-sectional view of the syringe of FIG. 1 with the plunger rod/protector and needle sheath attached.

FIG. 2 shows the syringe completely assembled and ready for shipment and long term storage. Elastomeric sheath 17 has been placed over needle 4 and frictionally attached to hub 3 at the sheath's open end. Plunger rod/protector 12 covers the needle, hub, sheath and outer surface 6. When plunger rod/protector 12 is so positioned, flexible protrusions 16 flex slightly to frictionally engage outer surface 6. Plunger rod/protector 12 has a cavity 7 between narrow portion 9 and attachment means 14 large enough so that the plunger rod/protector will not grip shoulder 17A when positioned.

To use the prefilled disposable syringe of FIG. 2, the operator removes plunger rod/protector 12 from its position covering the needle and engages engagement means 11 and 13. Next sheath 17 is removed and the injection is administered in the usual manner with plunger rod/protector 12 acting as a plunger rod for stopper 8.

Figure 3:
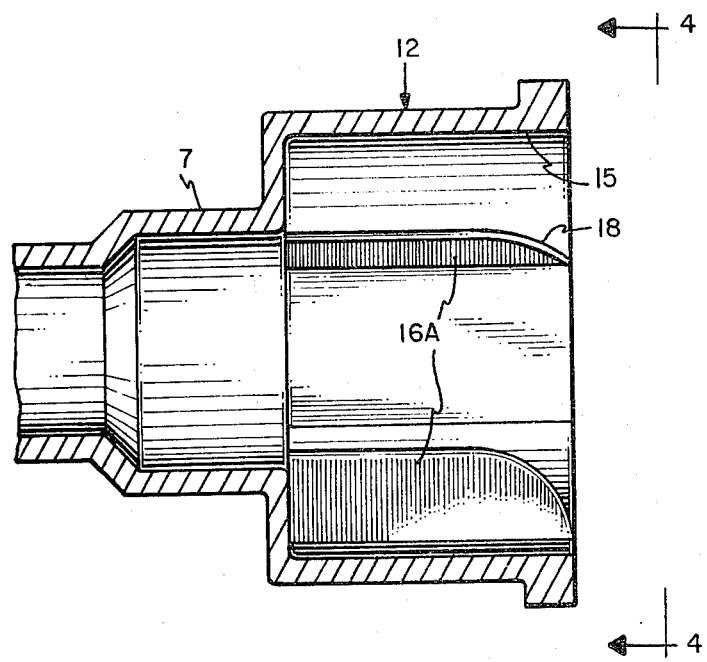
FIG. 3 is a partial cross-sectional view of a preferred embodiment of a plunger rod/protector in accordance with the invention taken in the longitudinal direction.
Figure 4:
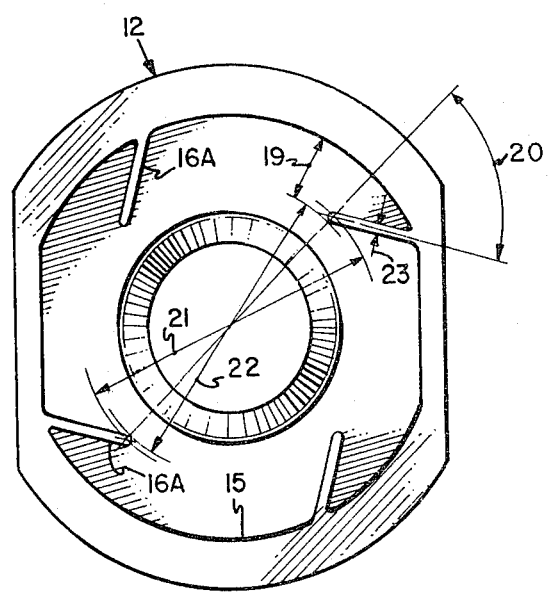
FIG. 4 is a view of the plunger rod/protector of FIG. 3 taken along lines 4—4.

FIG. 3 is a partial longitudinal cross-sectional view of a preferred embodiment of a plunger rod/protector in accordance with the invention. FIG. 4 is a view of FIG. 3 taken along lines 4—4. It is preferred that the outer surface of the barrel and inner surface 15 be substantially circular, but other shapes are acceptable. In FIGS. 3 and 4 the flexible means are flexible fins 16A disposed substantially axially to the needle (not shown). Fins 16A have rounded corners 18 on their extremity near the end of the plunger rod/protector for easier attachment to the outer surface of the barrel. Preferably the fins have depth 19 perpendicular to inner surface 15 of from about 0.14" to 0.17" (3.56 to 4.32 mm) with about 0.15" to 0.16" (3.81 to 4.06 mm) being most preferred. If the shield is made of plastic, it is preferable that the fins have thickness 23 of about 0.018" to 0.027", (0.46 to 0.69 mm) preferably about 0.022" to 0.025". (0.56 to 0.64 mm). It is especially preferred that thickness 23 increase gradually from about 0.02" (0.51 mm) at rounded corner 18 to about 0.025" (0.64 mm) at the end of fin 16A nearest to the cavity. Surprisingly, fins made to the preferred dimensions are easy to make, hold snugly, but are easy to disengage when desired, even after long term storage.

The length of fins 16A, measured in a direction parallel to the longitudinal axis of the syringe should be from 0.3" to 0.5" (7.62 to 12.7 mm) with about 0.375" (9.53 mm) being most preferred.

In FIG. 4, inner surface 15 is approximately circular. The outer surface of the barrel, shown in phantom having diameter 21, may be circular. Fins 16A are disposed in a preferred manner at equal distance around inner surface 15. The number of fins must be at least one, preferably at least four, with four being most preferred. Angle 20, the outer angle included between each fin and a radius drawn through the tip of each fin, may vary between 0° to 90°, with about 60° being preferred. In this instance, it is preferred that the diameter 21 of the outer surface of the barrel be about 0.425" (10.8 mm), and that diameter 22 of a circle connecting the inner most portion of the fins be about 0.38" to 0.400" (9.65 to 10.16 mm).

This invention has several advantages over prior art plunger rod/protectors that attach to the hub by an interference fit over the sheath. First, with the plunger rod/protector of this invention attached, the needle is far less likely to be accidently bent during shipment and handling. Secondly, with glass barrels, which are preferred for long term storage, the plunger rod/protector protects the barrel at the place where breakage is most likely to occur, that is, near the hub.

Frequently, to save time, it is desirable to remove the plunger rod/protector and engage it with the stopper before the operator (for example, a doctor or nurse) is ready to administer the injection. In a small percentage of cases, the prior art plunger rod/protector will pull the sheath from the needle when the plunger rod/protector is removed, thereby prematurely unsealing the needle, compromising sterility, and creating a danger of an exposed needle. Since the plunger rod/protector of the present invention does not attach by an interference fit over the sheath, the sheath will not be inadvertently removed when the plunger rod/protector is removed.

In a small percentage of cases, the prior art glass-covered-by-rubber-covered-by-plastic fit is too loose because of variation in size, particularly in the size of the glass hub. Glass is difficult to cast to close tolerance. The loose fitting plunger rod/protectors tend to slip off during shipment and handling. The flexible fins of the present invention are able to firmly attach directly to the glass surface, despite normal variations in the outer diameter of the barrel.

The present invention accomplishes all these advantages without using a special adapter on the barrel and without causing difficulty in removing the plunger rod/protector from its position covering the needle.

In addition to the prefilled, disposable syringe previously described, other embodiments of the invention that may find a commercial market are a disposable syringe suitable for prefilling comprising an assembly of hub, barrel and needle and a plunger rod/protector. The buyer of such syringe, who would furnish the medicament and stopper, would sterilize and prefill the syringe.

Furthermore, the plunger rod/protector of the present invention, by itself, may prove to be a salable quantity to a buyer who would supply the medicament, stopper and barrel-hub-needle assembly. Such a plunger rod protector should have an inner surface from which flexible means protrude that is larger than the outer surface of the narrow portion, so that attachment may be made to the barrel of a syringe for maximum protection.

What is claimed is:
1. A prefilled disposable syringe comprising:
   (a) an assembly comprising a hub, a needle rigidly attached to said hub, and a barrel having a hollow bore, said hollow bore in fluid communication with said needle, said barrel having an outer surface near said hub,
   (b) a stopper disposed in said bore having first engagement means,
   (c) medicament disposed in said bore between said stopper and said needle, and
   (d) a plunger rod/protector adapted to enclose said needle, hub and outer surface comprising a narrow portion having a cavity for said needle, said narrow portion capable of fitting within said hollow bore; attachment means for attaching said plunger rod/protector to said outer surface at a first end of said narrow portion comprising an inner surface adapted to enclose said outer surface and flexible means protruding from said inner surface to grip said outer surface; and a second engagement means at a second end of said narrow portion adpated to engage said first engagement means, wherein said plunger rod/protector is adapted to securely protect said needle during transit and storage and to act as a plunger rod after engagement of said firsrt and second engagement means.

2. The syringe of claim 1 wherein said barrel is glass.

3. The syringe of claim 2 wherein said flexible means comprise a plurality at flexible fins disposed substantially axially to said needle.

4. The syringe of claim 3 further comprising an elastomeric needle sheath adpated to cover and seal said needle and to attach to said hub by frictional fit at an open end, said sheath having a shoulder at said open end, and wherein said plunger rod/protector is adapted to cover said sheath and has a cavity between said narrow portion and said attachment means large enough to cover said shoulder without gripping said shoulder.

5. The syringe of claim 4 wherein said plunger rod/protector is constructed of material selected from the group consisting of polypropylene, polyethylene, polyamide, polyacrylonitrile, and copolymers thereof.

6. The syringe of claim 5 wherein said fins have depth perpendicular to said inner surface of from 0.14" to 0.17" and thickness of from 0.018" to 0.027".

7. The syringe of claim 6 wherein said inner surface has at least four fins disposed at substantially equal distance around said inner surface obliquely to said inner surface.

8. The syringe of claim 7 wherein said inner surface is approximately circular, and wherein said fins protrude from said inner surface such that an outer angle included between each of said fins and a radius of the circle drawn through the tip of each fin is about 60°.

9. A disposable syringe suitable for prefilling comprising:
   a. an assembly comprising a hub, a needle rigidly attached to said hub, and a barrel having a hollow bore, said hollow bore in fluid communication with said needle, said barrel having an outer surface near said hub, b. a plunger rod/protector adapted to enclose said needle, hub, and outer surface, comprising a narrow portion having a cavity for said needle, said narrow portion capable of fitting within said hollow bore, attachment means for attaching said plunger rod/protector to said outer surface at a first end of said narrow portion comprising an inner surface adapted to enclose said outer surface and flexible means protruding from said inner surface to grip said outer surface; and an engagement means at a second end of said narrow portion.

10. A plunger rod/protector comprising a narrow portion having an outer surface and a cavity, attachment means at a first end of said narrow portion comprising an enlarged inner surface, said inner surface being larger than said outer surface of said narrow portion and flexible means protruding from said inner surface adapted for attachment to an outer surface of a syringe barrel; and an engagement means at a second end of said narrow portion.

11. The plunger rod/protector of claim 10 wherein said flexible means comprises a plurality of flexible fins disposed axially to said hollow portion.

12. The plunger rod/protector of claim 11 further comprising a cavity between said narrow portion and said attachment means having size intermediate the size of said attachment means and the cavity in said narrow portion.

13. The plunger rod/protector of claim 12 constructed of material selected from the group consisting of polypropylene, polyethylene, polyamide, polyacylonitrite, and copolymers thereof.

14. The plunger/rod protector of claim 13 wherein said fins have depth perpendicular to said inner surface of from 0.14" to 0.17" and thickness of from 0.018" to 0.027".

15. The plunger rod/protector of claim 14 wherein said inner surface has at least 4 fins disposed at substantially equal distance around said inner surface, obliquely to said inner surface.

16. The plunger rod/protector of claim 15 wherein said inner surface is approximately circular, and wherein said fins protrude from said inner surface such that an outer angle included between each of said fins and a radius of the circle drawn through the tip of each fin is about 60°.

* * * * *